US011730969B1

(12) United States Patent
Vaughn et al.

(10) Patent No.: US 11,730,969 B1
(45) Date of Patent: Aug. 22, 2023

(54) TRANSCRANIAL MAGNETIC STIMULATION SYSTEM AND METHOD

(71) Applicant: Ampa Inc., San Diego, CA (US)

(72) Inventors: Donald A. Vaughn, San Diego, CA (US); Jonathan A. S. Downar, Carrying Place (CA)

(73) Assignee: AMPA INC., San Diego, CA (US)

( * ) Notice: Subject to any disclaimer, the term of this patent is extended or adjusted under 35 U.S.C. 154(b) by 0 days.

(21) Appl. No.: 17/964,686

(22) Filed: Oct. 12, 2022

(51) Int. Cl.
*A61N 2/00* (2006.01)
*A61N 2/02* (2006.01)
*A61B 5/055* (2006.01)

(52) U.S. Cl.
CPC .............. *A61N 2/006* (2013.01); *A61B 5/055* (2013.01); *A61N 2/02* (2013.01)

(58) Field of Classification Search
CPC .......... A61N 2/00; A61N 2/002; A61N 2/004; A61N 2/006; A61N 2/008; A61N 2/02
See application file for complete search history.

(56) References Cited

U.S. PATENT DOCUMENTS

| | | | |
|---|---|---|---|
| 6,132,361 A | 10/2000 | Epstein et al. | A61N 2/00 |
| 6,849,040 B2 | 2/2005 | Ruohonen et al. | A61N 1/00 |
| 7,824,324 B2 | 11/2010 | Riehl et al. | A61N 2/00 |
| 9,724,533 B1 | 8/2017 | Fischell et al. | A61N 2/008 |
| 9,968,798 B2 | 5/2018 | Fischell et al. | A61N 2/02 |
| 10,004,915 B2 | 6/2018 | Saitoh et al. | A61N 2/02 |
| 10,029,112 B1 | 7/2018 | Fischell et al. | A61N 2/02 |
| 10,137,308 B2 | 11/2018 | Adjouadi et al. | A61N 2/006 |
| 10,286,222 B2 * | 5/2019 | Nishikawa | A61N 2/008 |
| 10,507,335 B2 | 12/2019 | Zrenner et al. | A61N 2/02 |
| 11,000,693 B2 | 5/2021 | Ghiron | A61N 2/02 |
| 11,234,631 B2 | 2/2022 | Tucker | A61N 5/369 |
| 2004/0039279 A1 | 2/2004 | Ruohonen | A61B 5/05 |
| 2014/0179981 A1* | 6/2014 | Katz | A61B 90/361 600/15 |
| 2014/0343351 A1* | 11/2014 | Tojo | A61B 90/50 600/14 |
| 2016/0015588 A1* | 1/2016 | Tamiya | A61B 90/14 128/845 |
| 2016/0015995 A1* | 1/2016 | Leung | A61N 2/008 600/14 |
| 2016/0184601 A1* | 6/2016 | Gleich | A61N 2/02 600/14 |

(Continued)

FOREIGN PATENT DOCUMENTS

| | | | | |
|---|---|---|---|---|
| CN | 107648734 | * | 2/2018 | ............. A61N 2/006 |
| JP | 2003180649 | | 7/2003 | ............... A61B 5/05 |

(Continued)

*Primary Examiner* — Carrie R Dorna
(74) *Attorney, Agent, or Firm* — Hayes Soloway P.C.

(57) ABSTRACT

A transcranial magnetic stimulation system includes a magnetic field generator configured to generate a magnetic field to be applied to a patient's head, the magnetic field generator comprising one or more magnetic induction coils and a housing for the coils. One or more imaging devices configured to permit direct visualization of the coils on the patient's head are embedded in the housing. The one or more imaging device(s) may include one or more cameras, preferably one or more visible light imaging cameras, one or more ultraviolet light imaging cameras, or one or more infrared imaging cameras.

29 Claims, 9 Drawing Sheets

(56) References Cited

U.S. PATENT DOCUMENTS

| | | | | |
|---|---|---|---|---|
| 2017/0366773 | A1* | 12/2017 | Kiraly | ............... A61B 1/00006 |
| 2019/0060659 | A1* | 2/2019 | Ginhoux | ............... A61N 2/006 |
| 2020/0078599 | A1* | 3/2020 | Chen | ...................... A61N 2/006 |

FOREIGN PATENT DOCUMENTS

| | | | | |
|---|---|---|---|---|
| JP | 2004000636 | | 1/2004 | ............... A61B 5/05 |
| JP | 2006320425 | | 11/2006 | ............... A61B 5/05 |

\* cited by examiner

TRANSCRANIAL MAGNETIC STIMULATION SYSTEM AND METHOD

BACKGROUND OF THE DISCLOSURE

The present disclosure relates to a system for transcranial magnetic stimulation (TMS), i.e., methods and apparatus for positioning a transcranial magnetic stimulation device properly on the head of patients so as to deliver magnetic stimulation to a specific brain region. The disclosure has particular applicability to systems and methods for applying magnetic stimulation to target brain regions of a patient for treating depression and will be described in connection with such utility, although other utilities are FDA-approved including treatment for OCD, depression with comorbid anxiety, and nicotine addiction, and still others show promising early results including TMS for treatment of bipolar disorder, PTSD, eating disorders, personality disorders, alcohol and other substance use disorders, and autism, as well as neurological illnesses including Alzheimer's Disease and other dementias, migraine headaches, movement disorders such as Parkinson's Disease, tinnitus, and chronic pain.

For each of these disorders, a distinct set of brain regions is known to be functioning abnormally, and one or more of these regions must be located and accurately targeted during stimulation for successful treatment. In order to reliably stimulate a desired brain region, the TMS coil needs to be consistently and accurately placed at a target scalp location overlying that brain region, and must remain at that site throughout the entire stimulation session. Stimulation of off-target brain regions may reduce or eliminate the efficacy of the treatment, and in the worst case scenario may lead to worsening of symptoms, excessive pain during treatment, or rarely, a serious adverse event such as a seizure.

The process of positioning the TMS coil on the head, and maintaining it in place during treatment, is known as 'neuronavigation.' In current clinical practice, the most common approach to neuronavigation is to place a fabric cap on a patient's head, perform measurements of the head and scalp, and use these measurements to define a coordinate system (e.g., the '10-20 international encephalography system') which provides markers on the patient's head. A TMS operator would then use these marks to specify the target site on the cap, place the TMS coil over the marked target site, and then trace a (partial) outline of the coil on the cap for use in maintaining consistent coil orientation during treatment sessions, and from session to session. However, this method may be imprecise, and does not provide direct visual confirmation that the center of the coil is (1) directly over the target location, or (2) actually in physical contact with (i.e., touching) the patient's head.

In addition, patients may move during treatment and/or navigational aids may slip out of the desired position. If this occurs, the TMS technician must pause treatment, readjust position of the coil, and then resume stimulation. At worst, a patient can move his or her head in such a way that the TMS coil moves but is not observably positioned off target such that the session continues, with potential adverse consequences as identified above. Present methods lack a direct visual or other record confirming that (1) the TMS coil is optimally located over the desired target area, (2) the TMS coil remains over the desired target area throughout the stimulation session, and that (3) the TMS coil remains in physical contact with the surface of the patient's head during the entire session.

Figure 1:
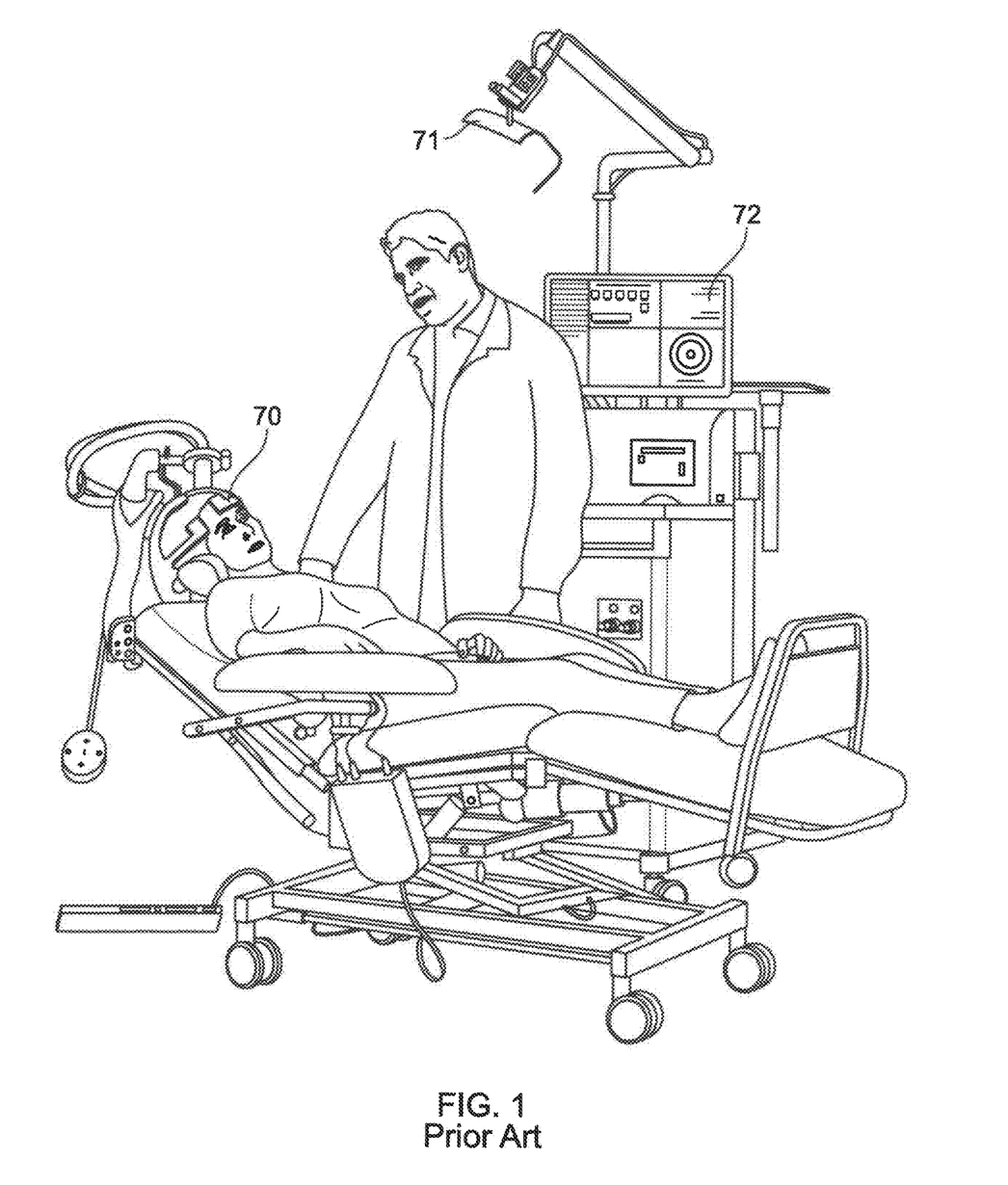
FIG. 1 is a schematic view of a conventional frameless stereotaxic MRI-guided neuronavigation system, in accordance with the prior art.
Figure 2:
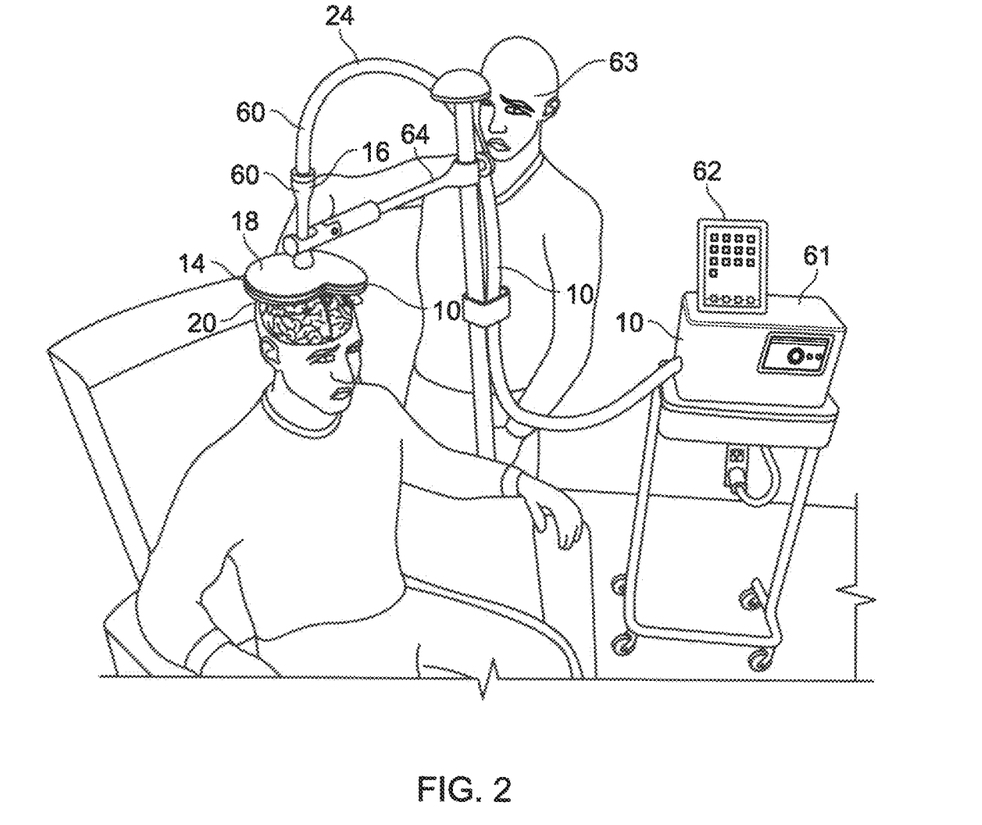
FIG. 2 is a schematic view of a TMS system in accordance with an embodiment of the instant disclosure.
Figure 3:
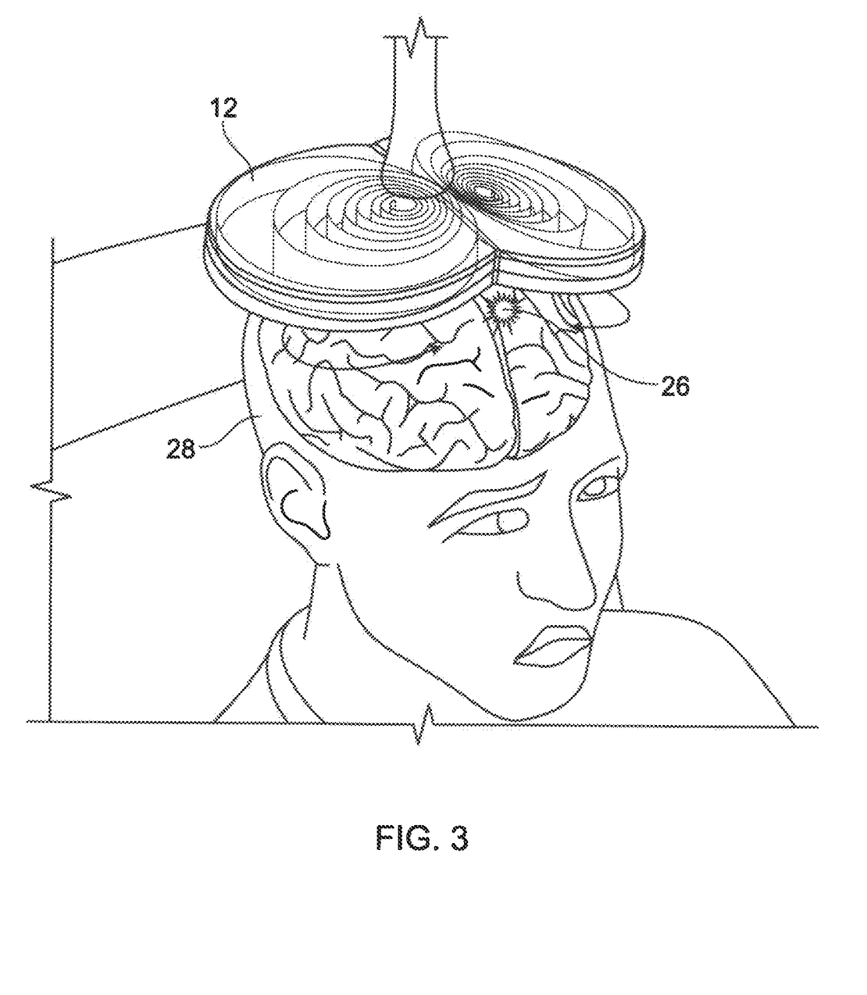
FIG. 3 is a schematic view of a TMS coil in accordance with an embodiment of the instant disclosure.

A more complex, less commonly used approach to neuronavigation (FIG. 1) involves a computerized frameless stereotaxic positioning system comprised of: (1) a set of optical position markers such as small reflective beads 70 attached in a specific 3-dimensional configuration to the coil as well as to a tracker on the patient's head, (2) a stereo camera 71 that visualizes and localizes the markers in 3-dimensional space, and (3) computer software 72 which uses 3-dimensional marker position information from the camera to impute the relative positions and orientations of the patient's head and the coil, and then provides a visualization of these positions on a screen viewed by the operator as a neuronavigation guide before and during treatment. Such a system usually, but not always, also includes (4) an MRI or other 3-dimensional image of the patient's head and brain, which the software aligns with the 3-dimensional imputed head position, so that the operator may visualize the brain region at the focus of the coil in real-time during coil positioning and treatment.

As examples, JP 2003-180649A and JP 2004-000636A disclose techniques for TMS coil neuronavigation using, for example, an optical tracking system employing infrared reflectors, as described above. This technology is commercially available and is also used in clinical settings such as neurosurgical procedures requiring neuronavigation.

JP 2006-320425A discloses another apparatus for positioning a TMS coil against the patient's head by using a multi jointed robot. This approach likewise has several major disadvantages, including the necessity of an MRI scan for every patient, the excessive additional expense and complexity of the apparatus itself, and the need for an operator to undergo an extended training period of several additional weeks to achieve proficiency in accurate use of the system. Further, the system can fail if: (1) the specified target is mistaken, (2) the markers on the coil are incorrectly calibrated, (3) following calibration, the markers on the patient's head move out of position during the session, (4) the operator is insufficiently skilled, or if (5) the coil is not quite in contact with the scalp despite appearing to be so on the neuronavigation system.

The complexity of this external tracking approach with MRI-guidance also greatly reduces the variety, and hence numerosity, of locations where patients may receive TMS treatment. This system is typically confined to a hospital setting because it requires high-field MRIs, as well as significant computing resources, specialized analysts to process the images, and technicians trained to competently operate the cumbersome neuronavigation suite. As a result, this approach is rarely used in the most accessible health care settings such as primary care clinics, mental health centers, assisted living facilities, outpatient specialty clinics, or workplace health centers. Instead, a patient seeking MRI-guided neuronavigated TMS is generally obliged to repeatedly travel to an academic or tertiary health care setting, raising additional barriers of cost and convenience and curtailing the accessibility of TMS treatment for those who need it.

The foregoing discussion of the prior art derives in part from U.S. Pat. No. 10,004,915 (the '915 Patent) wherein there is described a TMS system comprising a TMS alignment system comprising a means for generating magnetic field, the magnetic field generating means having a coil for generating a variable magnetic field to be applied to a certain part of patient's head and a holder for holding the coil; and a camera means for recognizing a predetermined reference marking made on a specific portion of the ear of the patient, (e.g., the tragus); the magnetic field generating means and the recognizing means being designed so that an alignment of the recognizing means with the marking causes the coil to be set in a proper posture with respect to the certain part of the patient's head.

According to the '915 Patent, with the aforesaid arrangement, the magnetic field generating means can be positioned with respect to the reference marking of a specific portion the patient's ear, allowing the user of the TMS system to position the magnetic field generating means without skill which is needed for conventional systems.

The recognition means of the '915 Patent includes at least one imaging device, i.e., cameras carried on external arms extending from an apparatus. Alignment includes aligning an optical axis of the imaging device with the marking. This allows that the coil is positioned in the proper posture with respect to the specific part of the patient.

Preferably, the TMS system of the '915 patent further comprises an optical device capable of emitting a directional beam, the optical device being provided adjacent the imaging device, wherein the alignment includes aligning an intersection of the optical axis of the optical device with the marking. This allows that the TMS coil is positioned in the proper position with respect to the specific part of the patient.

In another embodiment of the '915 Patent, the TMS system further comprises a moving mechanism for moving the coil holder on and along a surface of the patient's head; and a controlling means for controlling the moving mechanism in accordance with an output from the recognition means to automatically position the holder with respect against the marking.

As noted earlier, a problem with the TMS alignment system proposed in the '915 Patent is that the system requires marking directly on the patient, the system is bulky, and the arms required for holding the cameras or imaging devices are bulky and themselves prone to bending and/or misalignment. The alignment markings on the patient can also be obscured by the patient's hair. The additional components also bear the risk of inaccurately imputing the coil's actual position, as explained above. Lastly, the additional components reduce the overall accessibility of TMS treatment, by requiring technicians to undergo extensive additional training in order to operate the neuronavigation apparatus correctly, and by limiting treatment location to areas where a stationary multi-ton MRI scanner happens to reside.

SUMMARY

The present disclosure is based on the premise that major sources of potential error and uncertainty of treatment can be removed from the process of TMS coil neuronavigation if: (1) the target site on the head can continuously be precisely visualized under the center of the coil, and (2) a contact sensor can directly indicate whether the center of the TMS coil is in contact with the scalp during the entire stimulation session. In the present disclosure, we provide an optical scalp-landmarking approach which allows for much higher consistency in positioning a TMS coil over a given site on the scalp from session to session, as well as providing a direct visual record (as opposed to an imputed calculation) of whether the coil was properly positioned and maintained in this position and in contact with the scalp consistently throughout each session of stimulation. Said another way: rather than using externally-placed sensors and markers on the head to infer the coil location from an external perspective (as in FIG. 1), our approach uses sensors placed on the coil itself to, in essence, provide the coil's perspective. Moreover, since our novel approach allows the technician and supervising physician to directly visualize the target site while placing the coil, the time required to train a new technician to proficiency is greatly reduced, rather than extended. Moreover, a verifiable record of placement accuracy may be generated during each treatment session. Finally, our approach does not necessitate the use of costly and cumbersome additional components such as stereo cameras, MRI machines and intensive processing software, or reflector markers requiring calibration prior to treatment. This reduction in cost and complexity, as well as the marked acceleration of an operator's learning curve to proficiency, facilitates more widespread access to neuronavigated TMS treatment in a broader range of settings—outside the more limited number of specialized centers which host large, expensive apparatus, requiring extensive personnel.

In the present disclosure, we incorporate one or more imaging devices into a TMS coil so as to permit direct visualization of the placement of the center of the TMS coil on the head. In one embodiment, we incorporate a single camera directly in the center of the TMS coil so as to permit direct visualization of the area under a TMS coil. In another embodiment of the disclosure, we incorporate two or more cameras placed off-center and/or on the sides of the TMS coil. The camera(s) may comprise visual light imaging capabilities, ultraviolet light imaging capabilities or infrared light imaging capabilities.

In another embodiment, we also incorporate into the TMS coil one or more contact sensors so as to detect whether the patient's head is in contact with the coil before, during, and until the treatment session concludes. The contact sensors may comprise force-sensitive resistors, capacitive touch sensors, ultrasonic position/touch sensors, and/or thermal/infrared sensors.

In another embodiment, we also incorporate one or more imaging devices external to the coil, configured to allow for simultaneous visualization of the patient's head (and any associated markings) as well as the coil, as an independent measure of their relative positions. These additional coil-external cameras may comprise one or more cameras, LIDAR detectors, and/or ultrasonic detectors.

In one embodiment, we provide a specialized treatment cap having indicia with various markings including grid markings, text and/or color markings corresponding to specific anatomical locations on the head of the patient.

In another embodiment, the TMS system is configured to record and optionally, transmit, in real time, a video of the TMS coil placement during treatment. Also, in yet another embodiment, we include one or more accelerometers in the TMS coil so as to provide a supplementary record of the orientation of the TMS coil throughout treatment, so that the provider can detect any subtle drift or deviation of the coil during treatment, and make adjustments to the TMS coil orientation accordingly.

More particularly, in one aspect we provide a transcranial magnetic stimulation system comprising: a TMS system configured to generate a magnetic field to be applied to a patient's brain region, the TMS system comprising a transcranial magnetic stimulation (TMS) pulse generator as well as an inductor coil; and one or more imaging devices incorporated into the coil and configured to permit direct visualization of the TMS coil on the patient's head. The imaging device may comprise one or more cameras, preferably one or more visible light imaging cameras, one or more ultraviolet light imaging cameras, or one or more infrared imaging cameras.

The transcranial magnetic stimulation system may further comprise one or more accelerometers configured to sense orientation placement and/or changes in orientation of the TMS coil.

The transcranial magnetic stimulation system also may further comprise a memory device configured to create a video record of TMS coil placement during treatment.

We also provide a transcranial magnetic stimulation neuronavigation kit comprising the transcranial magnetic stimulation system as above described, and patient head cap having grid markings, text and/or color markings configured to overlie anatomical locations on the head of the patient. The patient head cap may include markings configured to overlie target areas of the head of the patient, and/or markings configured to permit continuous measurement of the position and orientation of the cap relative to the patient's head before, during, and after treatment.

BRIEF DESCRIPTION OF THE DRAWINGS

Further features of the disclosure will be seen from the following detailed description, taken in conjunction with the accompanying drawings, wherein.

DETAILED DESCRIPTION OF THE DISCLOSURE

As used herein the term transcranial magnetic stimulation (TMS) coil or coils shall mean the magnetic induction coils per se and their housing.

Referring to FIGS. 2-5, a neuronavigated transcranial magnetic stimulation system 10 in one embodiment includes one or more TMS coils, which itself consists of magnetic induction windings 12 in a housing 14 with leads in a cable 24. Alternatively, housing 14 may be connected to an inanimate support mechanism. Housing 14 includes a handle 16 sized for a human hand. Housing 14 includes a top surface 18 and a bottom surface 20, which can be arched to facilitate closer mating with the head of a patient.

The neuronavigated transcranial magnetic stimulation system 10 also includes a pulse generator 61 with an internal control unit and associated power source. The pulse generator sends electricity to windings 12 through a cable 24. The pulse generator 61 may be configured to communicate with smartphone, tablet or PC 62 having a program for the device to send parameters to the pulse generator 61 or for the device to receive data back from the pulse generator. The neuronavigated transcranial magnetic stimulation system 10 is designed to treat and/or ease certain symptoms by applying magnetic stimulation with a certain intensity and frequency through a patient's skull to a target area 26 in the brain within the patient's skull 28. The coil 60 may be held in place by an operator 63, coil-holder 64, or both.

Figure 4:
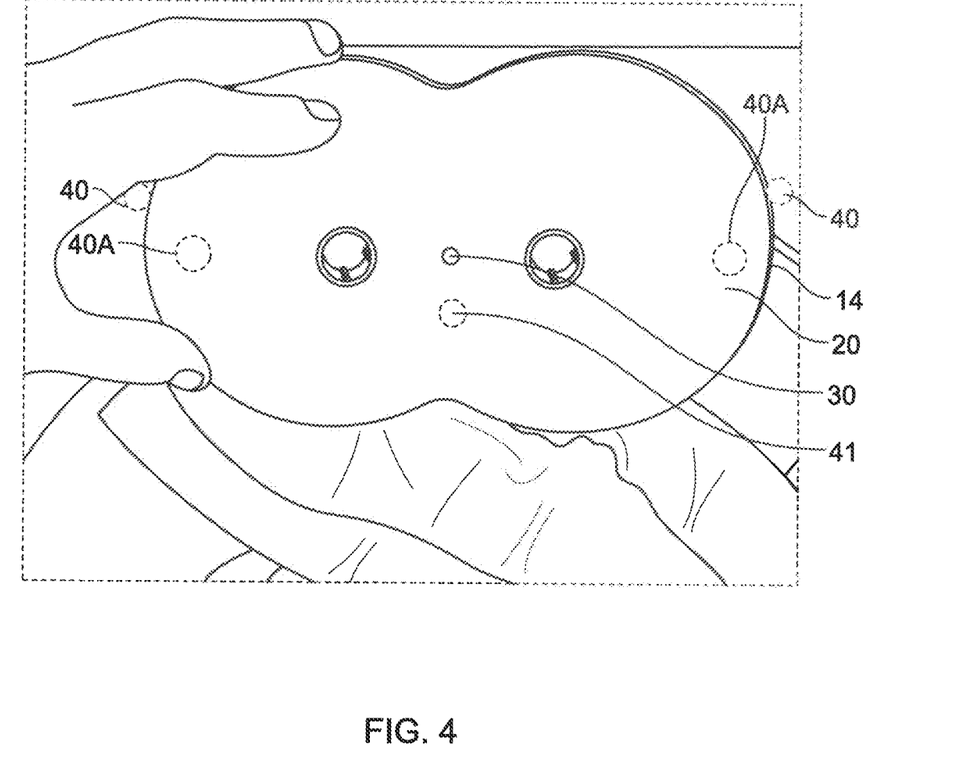
FIG. 4 is a bottom plan view of a TMS coil element of the present disclosure.
Figure 5:
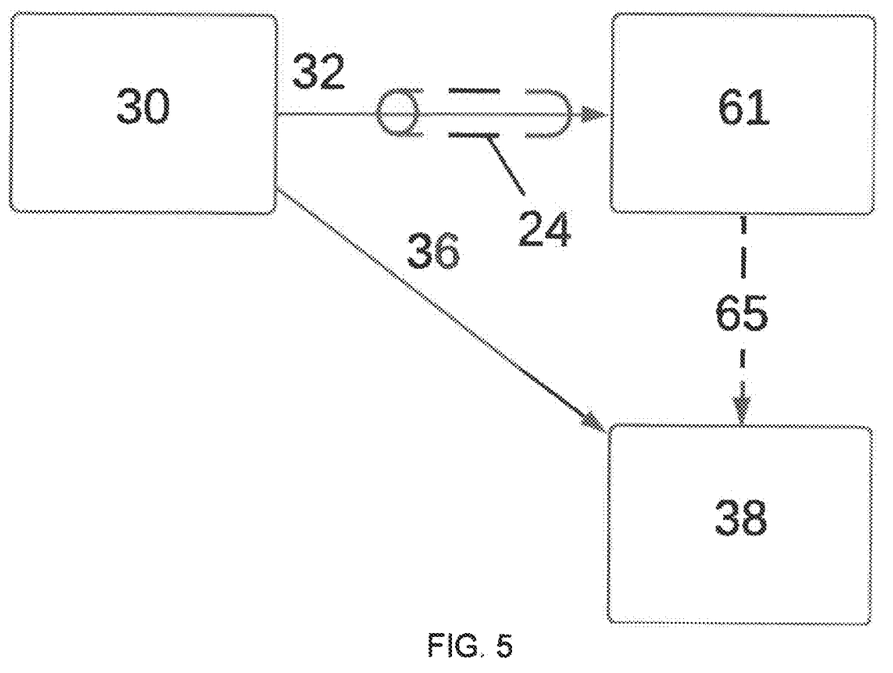
FIG. 5 is a block diagram of a power and control circuit of the present disclosure.

Referring in particular to FIG. 4, housing 14 includes an imaging device 30 configured to face downward from bottom surface 20, i.e., towards the head of a patient when in use, to permit direct visualization of the patient's head. In one embodiment, an imaging device 30 is located centrally relative to the magnetic induction coils. Imaging device 30 preferably comprises a camera which may be a visual light imaging camera, an ultraviolet light imaging camera or an infrared imaging camera. Referring in particular to FIG. 5, in one embodiment, imaging device 30 is connected via cable 36 to a display and memory device 38 which may be a smartphone, tablet or PC. In another embodiment, imaging device 30 is connected via a cable 32 to the pulse generator 61. Cable 32 may travel through cable 24. Optionally, pulse generator 61 may pass imaging information to device 38 which may be a smartphone, tablet or PC. This connection 65 may be wired, or wireless via Bluetooth, Wi-Fi, NFC or the like.

Alternatively, as shown in phantom at 40, the imaging devices may include spaced imaging devices located away from the center, at the sides of the magnetic induction coil's windings 12. Alternatively, two or more imaging devices shown in phantom at 40A, may be placed facing downward, away from the center of the housing, but within the housing, spaced from one another at the same distance from the center of the windings 12, or attached adjacent to the edges of the windings 12.

Also, if desired, one or more contact sensors 41 configured to detect force between the coils and the patient's head may be provided, carried on the underside of housing 14. The contact sensors 41 may comprise one or more force-sensitive sensors, one or more capacitive sensors, or one or more infrared sensors.

Figure 6A:
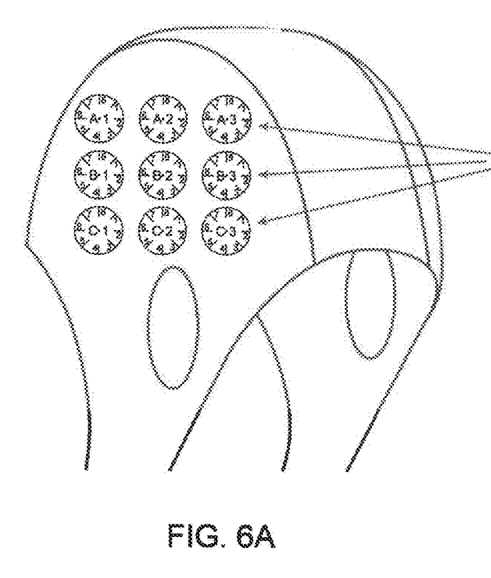
FIGS. 6A and 6B are perspective views of a cap element of the present disclosure.
Figure 6B:
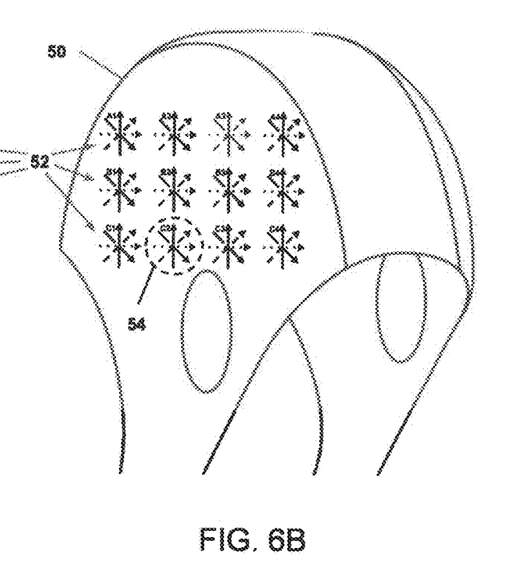
Figure 7A:
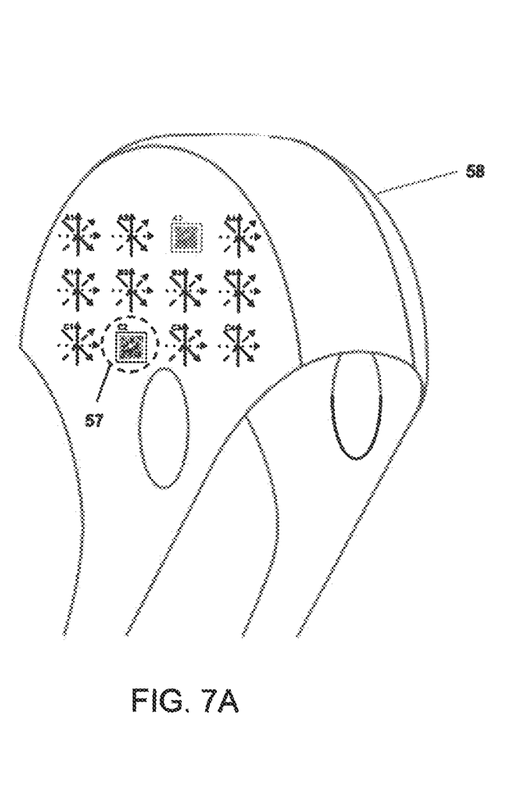
FIGS. 7A and 7B are perspective views of alternative cap elements of the present disclosure.
Figure 7B:
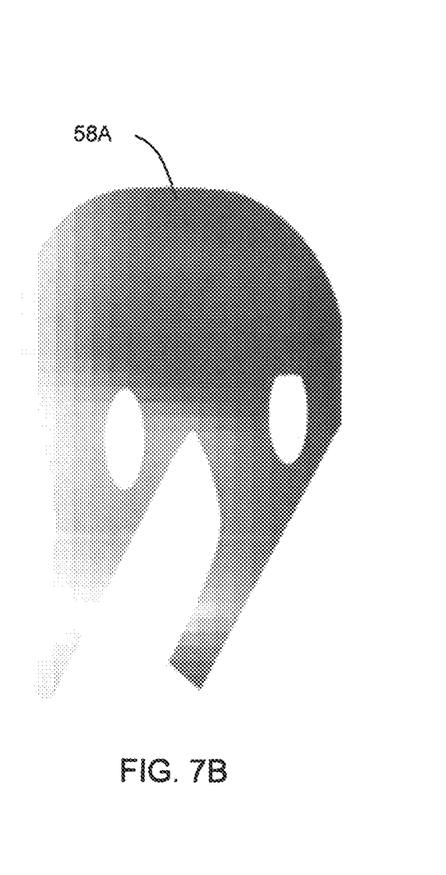

Referring also to FIG. 6, in a preferred embodiment of the disclosure, we provide a treatment cap 50 sized and shaped to fit snugly over a patient's head. The cap may be composed of material intentionally designed to stretch, to accommodate a defined range of head sizes slightly larger than its unstretched size. Preferably cap 50 may be provided in a kit with several different sizes to fit different size patients. Typically five sizes are sufficient to fit the majority of adult heads, a sixth size for youths, and a seventh size for small children and infants. Cap 50 includes indicia 52 in the form of a specific grid with anatomical markers printed on the cap. The indicia or markers may include text, color and/or symbols to identify specific target locations in the head of the wearer and/or shapes and patterns to indicate orientation for the TMS windings 12 to facilitate the magnetic induction in the correct location and orientation. These indicia may also be comprised of symbols, QR codes, color spectra, or any combination thereof. The indicia may be identical across numerous copies of the cap produced. Alternatively, a cap 50 may instead have unique indicia 57 in one or more locations such that the cap and any location on it can be uniquely distinguished from any other (FIG. 7A). Alternatively, the cap 58A may have printed patterns or color gradations to guide placement. The caps also may include indicia to personalize a cap to an individual patient.

Because the magnetic induction coil's field has a particular orientation (it is directional, not symmetric), the angle at which the magnetic induction coil is placed over a given location makes a meaningful difference in how patients experience the procedure. Specifically, even over the exact same central location, positioning the coil at different angles will activate different central and peripheral nerves. In the latter case, this may cause uncomfortable sensations at some angles, but not others. For example, at some angles, a patient's jaw may jitter during TMS, while not at others. Thus, the indicia's shape and pattern uniquely identifies each angle at which the magnetic induction coil may be placed so that, in conjunction with the camera, a viewer can see if they are properly and consistently aligned. Notably, the indicia are neither radially, nor bilaterally symmetric, and thus a rotation of 180 degrees of the magnetic induction coil will result in a different perspective on any given marker so that it is again, uniquely identified. Similarly, the text and color combination of each anatomical marking uniquely identifies the location. Locations commonly used as stimulation targets or reference locations in the therapeutic TMS community are further differentiated using color, to allow for quick and robust setup. This permits the healthcare provider to ensure that the magnetic induction windings 12 are properly positioned on the head of the wearer, and not skewed or tilted. We also can infer the coil's distance from the head of the wearer due to image size, to ensure that the coil is in full contact when seen by the imaging device.

Figure 8A:
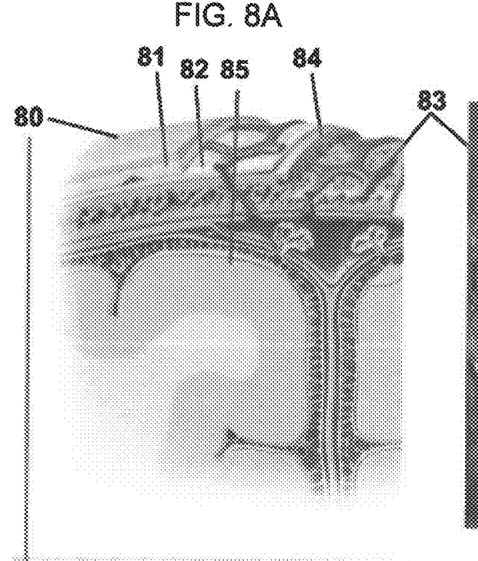
FIGS. 8A-8C are views of a patient's skin, vasculature, bone, and cortical elements of the head.
Figure 8B:
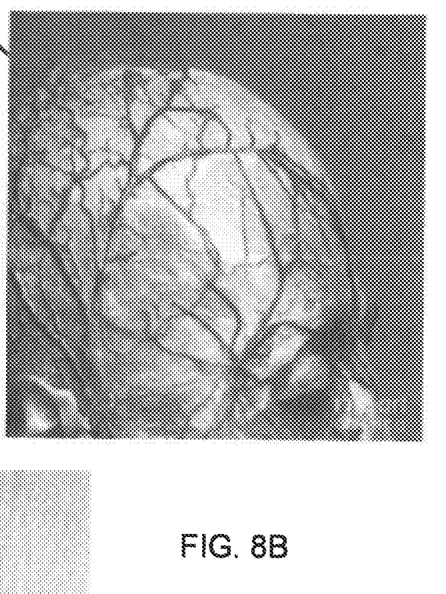
Figure 8C:
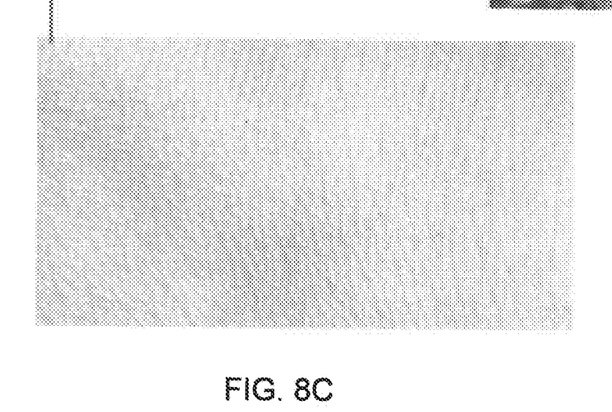

In another embodiment no specialized treatment cap is employed. Instead, patient-specific anatomical features are used to locate and maintain the coil in position. Referring to FIGS. 8A-8C, these features may comprise the epidermis 81, dermis 82 and hypodermis 82 patterns, scalp vascularization 83, bone density 84 and neural tissue configuration 85 obtained by an optical or infrared camera and/or through functional near infrared spectroscopy.

This makes it possible to perform a multi-modal "fingerprint" of the precise location of the stimulation target and determine the location of the magnetic induction coil accordingly based on these individually unique anatomical features of each patient's scalp itself rather than the pre-marked cap. The image patterns may be recorded and saved for future treatments.

Figure 9:
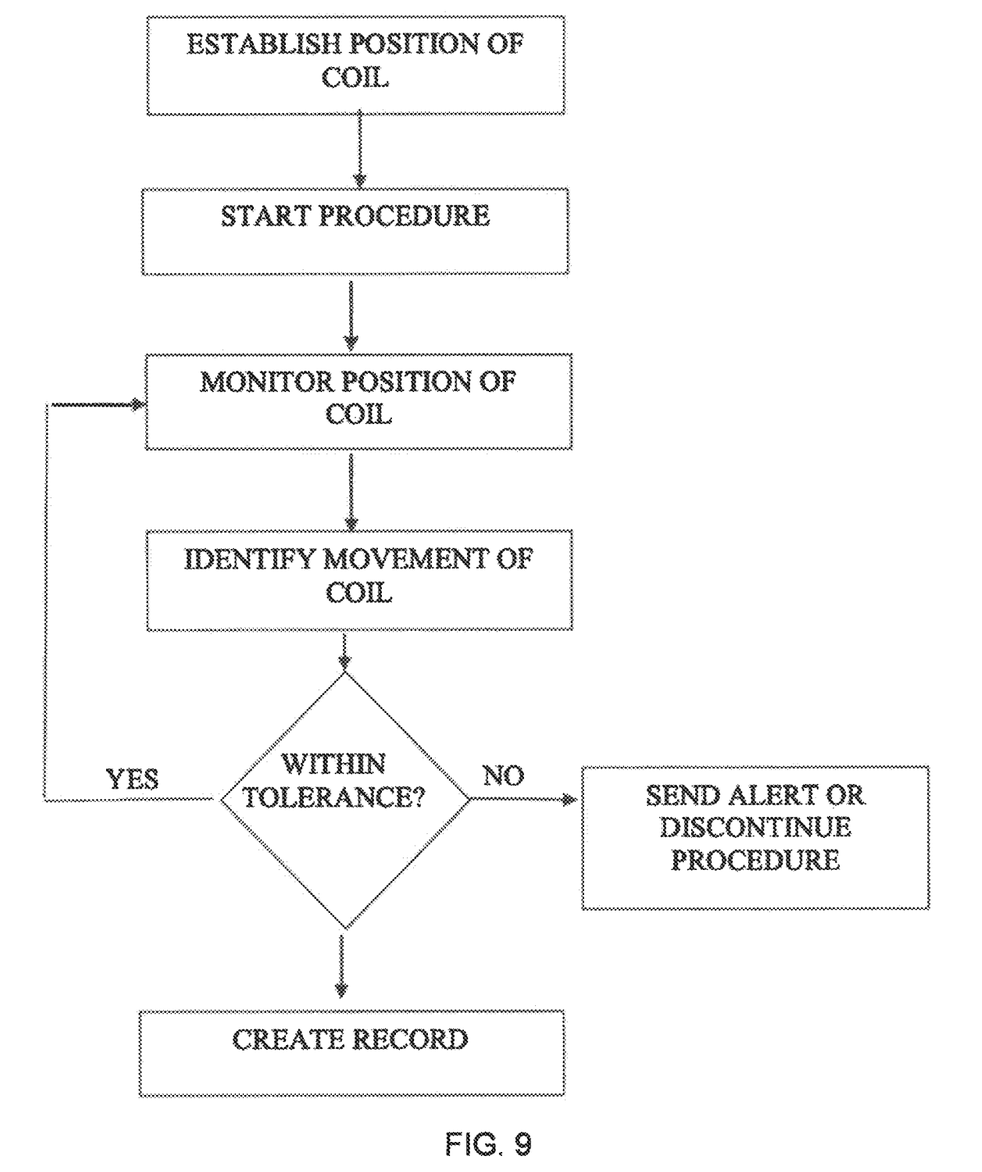
FIG. 9 is a flow diagram of a method of the present disclosure.

A feature and advantage of the present disclosure derives from use of one or more imaging devices internal to the TMS coil housing 14 which not only ensures proper placement of the transcranial magnetic stimulation system, but also permits continuous monitoring of placement and also includes an ability to record and/or transmit placement data in real time during the entire procedure. Also, by providing target indicia 54 on the cap, the healthcare provider can accurately locate the transcranial magnetic stimulator over a target area of the brain. Alignment can be prompted via visual, auditory and/or haptic feedback. Referring to FIG. 9, another feature and advantage of the present disclosure that results from the use of built-in imaging devices is that, should the coil be dislodged or moved (due to movement by the patient for example), an alert signal can be generated for the health care provider. Moreover, to protect the patient from possible harm, the magnetic stimulator can be programmed to not start until the magnetic induction coil is properly positioned, and to turn off or pause delivery of stimulation pulses when misalignment of the magnetic induction coil exceeds a certain tolerance, prompting correction of the position by the operator before proceeding.

Various changes may be made in the foregoing disclosure. Still other changes may be made without departing from the spirit and scope thereof.

What is claimed:

1. A neuronavigated transcranial magnetic stimulation system comprising:

i) a pulse generator;

ii) two transcranial magnetic stimulation (TMS) coils side-by-side in a housing and configured to be placed over a target brain region of a patient's head for treatment; and iii) one or more imaging devices including a single camera central to centers of the TMS coils and configured to permit direct visualization of a position of the TMS coils relative to a target position on the patient's head, wherein the single camera and the centers of the TMS coils are all colinear.

2. The neuronavigated transcranial magnetic stimulation system of claim 1, wherein the one or more imaging devices comprises one or more cameras, including the single camera colinear with the centers of the TMS coils.

3. The neuronavigated transcranial magnetic stimulation system of claim 2, wherein the one or more imaging devices comprises one or more visible light imaging cameras, one or more ultraviolet light imaging cameras or one or more infrared imaging cameras.

4. The neuronavigated transcranial magnetic stimulation system of claim 3, wherein the one or more imaging devices are configured to transmit an image of the patient's scalp vasculature, the patient's skin patterns, the patient's skull bone structure, or the patient's brain tissue, as a case may be.

5. The neuronavigated transcranial magnetic stimulation system of claim 2, wherein the one or more imaging devices also comprises two or more cameras located to sides of the TMS coils.

6. The neuronavigated transcranial magnetic stimulation system of claim 2, wherein the one or more imaging devices also comprises two or more cameras located away from the center but within the housing of the TMS coils.

7. The neuronavigated transcranial magnetic stimulation system of claim 1, further comprising one or more accelerometers configured to sense orientation placement or changes in orientation of the TMS coils.

8. The neuronavigated transcranial magnetic stimulation system of claim 1, further comprising one or more contact sensors configured to detect contact and force between the TMS coils and the patient's head.

9. The neuronavigated transcranial magnetic stimulation system of claim 8, wherein the contact sensors comprise one or more force-sensitive resistors, one or more capacitive touch sensors, or one or more ultrasonic position/touch sensors.

10. The neuronavigated transcranial magnetic stimulation system of claim 1, further comprising one or more imaging devices external to the TMS coils, and configured to permit simultaneous visualization of the patient's head as well as the TMS coils.

11. The neuronavigated transcranial magnetic stimulation system of claim 10, wherein the one or more imaging devices external to the TMS coils comprises one or more cameras, one or more LIDAR detectors, or one or more ultrasonic detectors.

12. The transcranial magnetic stimulation system of claim 1, further comprising a memory device configured to create a record of the TMS coils position before and during treatment.

13. A transcranial magnetic stimulation kit comprising a transcranial magnetic stimulation system, comprising:

i) a pulse generator;

ii) two transcranial magnetic stimulation (TMS) coils in a housing and configured to be placed over a target brain region of a patient for treatment;

iii) one or more imaging devices including a single camera central to centers of the TMS coils and configured to permit direct visualization of a position of the TMS coils relative to a target position on the patient's head, wherein the single camera and the centers of the TMS coils are all colinear; and (iv) a patient head cap having at least one of grid markings, text and color markings configured to overlie anatomical locations on the head of the patient.

14. The transcranial magnetic stimulation kit of claim 13, including markings configured to overlie target areas of the head of the patient.

15. The transcranial magnetic stimulation kit of claim 13, including markings configured to permit continuous measurement of the relative position and orientation of the cap versus the patient's head before, during, and after treatment.

16. The neuronavigated transcranial magnetic stimulation kit of claim 13, wherein the one or more imaging devices comprises one or more cameras, including the single camera central to the centers of the TMS coils.

17. The neuronavigated transcranial magnetic stimulation kit of claim 16, wherein the one or more imaging devices comprises one or more visible light imaging cameras, one or more ultraviolet light imaging cameras or one or more infrared imaging cameras.

18. The neuronavigated transcranial magnetic stimulation kit of claim 17, wherein the one or more imaging devices are configured to transmit an image of the patient's scalp vasculature, the patient's skin patterns, the patient's skull bone structure, or the patient's brain tissue, as a case may be.

19. The neuronavigated transcranial magnetic stimulation kit of claim 16, wherein the one or more imaging devices also comprises two or more cameras located to sides of the TMS coils.

20. The neuronavigated transcranial magnetic stimulation kit of claim 16, wherein the one or more imaging devices also comprises one or more cameras located away from the center but within the housing of the TMS coils.

21. The neuronavigated transcranial magnetic stimulation kit of claim 13, further comprising one or more contact sensors configured to detect contact and force between the TMS coils and the patient's head.

22. The neuronavigated transcranial magnetic stimulation kit of claim 13, further comprising one or more accelerometers configured to sense orientation placement or changes in orientation of the TMS coils.

23. The neuronavigated transcranial magnetic stimulation kit of claim 21, wherein the one or more contact sensors comprises one or more force-sensitive resistors, one or more capacitive touch sensors, or one or more ultrasonic position/touch sensors.

24. The neuronavigated transcranial magnetic stimulation kit of claim 13, further comprising one or more imaging devices external to the two TMS coils, and configured to permit simultaneous visualization of the patient's head as well as the TMS coils.

25. The neuronavigated transcranial magnetic stimulation kit of claim 13, wherein the one or more imaging devices comprises one or more cameras including the single camera central to the centers of the TMS coils, one or more LIDAR detectors, or one or more ultrasonic detectors.

26. The transcranial magnetic stimulation kit of claim 13, further comprising a memory device configured to create a record of the TMS coil(s) position before and during treatment.

27. A method for stimulating a target brain region by transcranial magnetic stimulation, which method comprises:
   i) providing the neuronavigated transcranial magnetic stimulation system including two transcranial magnetic stimulators (TMS) coils within a housing and configured to be placed over the target brain region of a patient's head, wherein the system includes one or more imaging devices including a single camera central to centers of the TMS coils and configured to permit direct visualization of the TMS coil(s) relative to a target position on the patient's head, wherein the single camera and the centers of the TMS coils are all colinear;
   ii) positioning the TMS coils over the target brain region using the single camera central to the center of the TMS coils to permit direct visualization and placement of the TMS coils over the target position; and
   iii) activating and deactivating the TMS coil(s) according to a treatment protocol.

28. The method of claim 27, including the step of providing the patient with a head cap having indicia markings in the form of at least one of a grid, text and color markings configured to overlie anatomical locations on the head of the patient; and
   positioning the TMS coils over the target brain region using the one or more imaging devices to visualize placement of the TMS coils relative to the indicia.

29. The transcranial magnetic stimulation kit of claim 13, further comprising a memory device configured to create a record of the TMS coils position before and during treatment.

* * * * *